US012655117B2

(12) United States Patent
Borate et al.

(10) Patent No.: US 12,655,117 B2

(45) Date of Patent: Jun. 16, 2026

(54) PREPARATION OF SUBSTITUTED AROMATIC CARBOXAMIDES

(71) Applicant: BASF SE, Ludwigshafen (DE)

(72) Inventors: Kailaskumar Borate, Navi Mumbai (IN); Bernd Wolf, Ludwigshafen (DE); Florian Vogt, Ludwigshafen (DE); Christopher Koradin, Ludwigshafen (DE); Roland Goetz, Ludwigshafen (DE); Harish Shinde, Navi Mumbai (IN)

(73) Assignee: BASF SE, Ludwigshafen (DE)

( * ) Notice: Subject to any disclaimer, the term of this patent is extended or adjusted under 35 U.S.C. 154(b) by 1053 days.

(21) Appl. No.: 17/779,262

(22) PCT Filed: Nov. 25, 2020

(86) PCT No.: PCT/EP2020/083279

§ 371 (c)(1),
(2) Date: May 24, 2022

(87) PCT Pub. No.: WO2021/110498

PCT Pub. Date: Jun. 10, 2021

(65) Prior Publication Data

US 2023/0028964 A1 Jan. 26, 2023

(30) Foreign Application Priority Data

Dec. 5, 2019 (EP) .................................... 19213739
Feb. 25, 2020 (EP) .................................... 20159309

(51) Int. Cl.
*C07D 271/06* (2006.01)

(52) U.S. Cl.
CPC .................................. *C07D 271/06* (2013.01)

(58) Field of Classification Search
CPC .................................................... C07D 271/06
See application file for complete search history.

(56) References Cited

U.S. PATENT DOCUMENTS

| | | | |
|---|---|---|---|
| 5,631,401 | A | 5/1997 | Stein et al. |
| 2011/0054183 | A1 | 3/2011 | Reichert et al. |

FOREIGN PATENT DOCUMENTS

| | | | |
|---|---|---|---|
| WO | WO-2009/135860 A1 | 11/2009 | |
| WO | WO-2015/185485 A1 | 12/2015 | |
| WO | WO-2017/211649 A1 | 12/2017 | |
| WO | WO-2017/211652 A1 | 12/2017 | |

OTHER PUBLICATIONS

Gayo et al., Ion-exchange resins for solution phase parallel synthesis of chemical libraries, Tetrahedron Letters, 38(4):513-6 (Jan. 1997).

International Application No. PCT/EP2020/083279, International Search Report and Written Opinion, mailed Feb. 4, 2021.

European Search Report for EP Patent Application No. 19213739.6, Issued on Jun. 12, 2020, 3 pages.

*Primary Examiner* — Shawquia Jackson
(74) *Attorney, Agent, or Firm* — MARSHALL, GERSTEIN & BORUN LLP

(57) ABSTRACT

The present invention relates to a process for the preparation of substituted aromatic carboxamides of formula I, (formula I) which can be obtained through reaction of an aromatic carboxylic acid halide and an amine, whereas the process is conducted in the absence of an auxiliary base in a carboxylic acid ester as solvent.

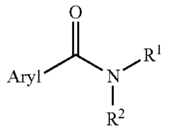

I

12 Claims, 3 Drawing Sheets

PREPARATION OF SUBSTITUTED AROMATIC CARBOXAMIDES

CROSS-REFERENCE TO RELATED APPLICATIONS

This is the U.S. national phase of International Application No. PCT/EP2020/083279, filed Nov. 25, 2020, which claims the benefit of European Patent Application No. 19213739.6, filed Dec. 5, 2019, and European Patent Application No. 20159309.2, filed Feb. 25, 2020.

The present invention relates to a process for the preparation of substituted aromatic carboxamides of formula I,

I

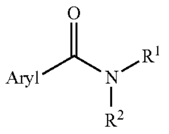

which can be obtained through reaction of an aromatic carboxylic acid halide and an amine, whereas the process is conducted in the absence of an auxiliary base in a carboxylic acid ester as solvent.

The process is particularly useful for the synthesis of 3-aryl-5-trifluoromethyl-1,2,4-oxadiazoles bearing a carboxamide moiety attached to the 3-aryl ring. Substituted 3-aryl-5-trifluoromethyl-1,2,4-oxadiazoles are known to be useful for controlling phytopathogenic fungi, for example from WO 2015/185485 A1 and WO 2017/211649 A1.

Transformations involving the reaction of aromatic carboxylic acid derivatives and amines to produce carboxamides are well known. Typically, these transformations employ an activated carboxylic acid, for example a carboxylic acid chloride, which is reacted with an amine in the presence of at least stoichiometric amounts of an auxiliary base in a solvent.

US 20110054183 describes a process, which is particularly useful on an industrial scale as it does not require the presence of a base and is conducted at reduced pressure and at refluxing conditions in solvents such as aromatic hydrocarbons, for example, toluene, ortho-, meta-, or para-xylene. The authors demonstrate in working examples 1a-3 that the amine must be slowly metered into a solution of the acid halide, preferably within 3 to 5 hours. Faster addition leads to diminished yields. The slow addition ensures that the hydrogen chloride, which is formed upon reaction, can escape the reaction vessel under vacuum in order to prevent the formation of the hydrochloride salt with the amine reactant, especially in the absence of an auxiliary base. Formation of said hydrochloride salt reduces the reactivity of the amine towards the acid halide and thus prevents the fast and complete conversion of the acid halide.

There is a constant need for improved and more economical processes, which enable the preparation of carboxamides of formula I on an industrial scale in high yield and with low amounts of residual starting material or unwanted side-products. In view of the prior art mentioned above, it was an object of the present invention to overcome the disadvantages of these processes.

The process of the present invention differs from the processes disclosed in the prior art mentioned above by making use of carboxylic acid esters as solvent. The inventors surprisingly found that, under the conditions of the process of the present invention, the amine reactant may be added in a much shorter period of time than previously reported, while at the same time allowing for the complete conversion of the starting materials to produce the carboxamides in high purity and excellent yields. Moreover, the process requires lower reaction temperatures.

Thus, the process of the present invention is more cost efficient and more eco-friendly than previously reported processes through the use of a solvent, which is ecologically benign, cheaper and less toxic than the solvents described in the prior art.

Accordingly, the present invention relates to a process for preparing an aromatic carboxamide of formula I,

I

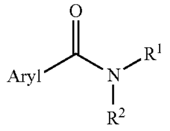

wherein

Aryl is phenyl or a 5- or 6-membered aromatic heterocycle; wherein the ring member atoms of the aromatic heterocycle include besides carbon atoms 1, 2, 3, or 4 heteroatoms selected from N, O, and S as ring member atoms with the provision that the heterocycle cannot contain 2 contiguous atoms selected from O and S; and wherein Aryl is further unsubstituted or further substituted with additional n identical or different radicals $R^A$; wherein n is 0, 1, 2, 3, or 4;

$R^A$ is independently selected from the group consisting of cyano, 5-(trifluoromethyl)-1,2,4-oxadiazole-3-yl, halogen, $C_1$-$C_6$-alkyl, $C_1$-$C_6$-haloalkyl, $C_1$-$C_6$-alkoxy, and $C_1$-$C_6$-haloalkoxy;

$R^1$ is $C_1$-$C_6$-alkyl, $C_1$-$C_6$-alkoxy, $C_3$-$C_{11}$-cycloalkyl, $C_3$-$C_3$-cycloalkenyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_6$-alkylamino, di$C_1$-$C_6$-alkylamino, —C(═O)—($C_1$-$C_6$-alkyl), —C(═O)—($C_1$-$C_6$-alkoxy), phenyl-$C_1$-$C_4$-alkyl, phenyl-$C_1$-$C_4$-alkenyl, phenyl-$C_1$-$C_4$-alkynyl, heteroaryl-$C_1$-$C_4$-alkyl, phenyl, naphthyl, or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein the heteroaryl group in the group heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O, and S as ring member atoms with the provision that the heterocycle cannot contain 2 contiguous atoms selected from O and S; and wherein any of the above-mentioned aliphatic or cyclic groups are unsubstituted or substituted with 1, 2, 3, or up to the maximum possible number of identical or different groups $R^{1a}$; or $R^1$ and $R^2$, together with the nitrogen atom to which they are attached, form a saturated or partially unsaturated mono- or bicyclic 3- to 10-membered heterocycle, wherein the heterocycle includes beside one nitrogen atom and one or more carbon atoms no further heteroatoms or 1, 2 or 3 further heteroatoms independently selected from N, O, and S as ring member atoms with the provision that the heterocycle cannot contain 2 contiguous atoms selected from O and S; and wherein the heterocycle is unsubstituted or substituted with 1, 2, 3, 4, or up to the maximum possible number of identical or different groups $R^{1a}$; wherein $R^{1a}$ is halogen, oxo, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, —$NHSO_2$—$C_1$-$C_4$-alkyl, (C=O)—($C_1$-$C_4$-alkyl), C(=O)—($C_1$-$C_4$-alkoxy), $C_1$-$C_6$-alkylsulfonyl, hydroxy$C_1$-$C_4$-alkyl, C(=O)—$NH_2$, C(=O)—NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl, or $C_1$-$C_4$-alkoxy-$C_1$-$C_4$-alkyl;

$R^2$ is hydrogen, $C_1$-$C_6$-alkyl, $C_2$-$C_6$-alkenyl, $C_2$-$C_6$-alkynyl, $C_1$-$C_6$-alkoxy, $C_3$-$C_{11}$-cycloalkyl, —C(=O)H, —C(=O)—($C_1$-$C_6$-alkyl), —C(=O)—($C_3$-$C_{11}$-cycloalkyl), or —C(=O)—($C_1$-$C_6$-alkoxy); and wherein any of the aliphatic or cyclic groups in $R^2$ are unsubstituted or substituted with 1, 2, 3, or up to the maximum possible number of identical or different radicals selected from the group consisting of halogen, hydroxy, oxo, cyano, $C_1$-$C_6$-alkyl, $C_1$-$C_6$-alkoxy, and $C_3$-$C_{11}$-cycloalkyl;

the process comprising the following steps:

step 1: charging a reaction vessel with a solvent and an aromatic carboxylic acid halide of formula II, Aryl-C(=O)—Hal II wherein Aryl is as defined above for compounds of formula I and Hal is fluorine, chlorine or bromine;

step 2: establishing a pressure of from 10 to 70 kPa in the reaction vessel;

step 3: metering in an amine compound of formula III;

$HNR^1R^2$ III wherein $R^1$ and $R^2$ are as defined above for compounds of the formula I; and, optionally, step 4: isolating the compound of formula I;

whereas the process is conducted in the absence of an auxiliary base and is characterized in that the solvent is selected from a carboxylic acid ester of formula V, $R^X$—C(=O)—O—$R^Y$ V wherein $R^X$ is methyl, ethyl or propyl; $R^Y$ is $C_1$-$C_6$-alkyl.

Figure 1:
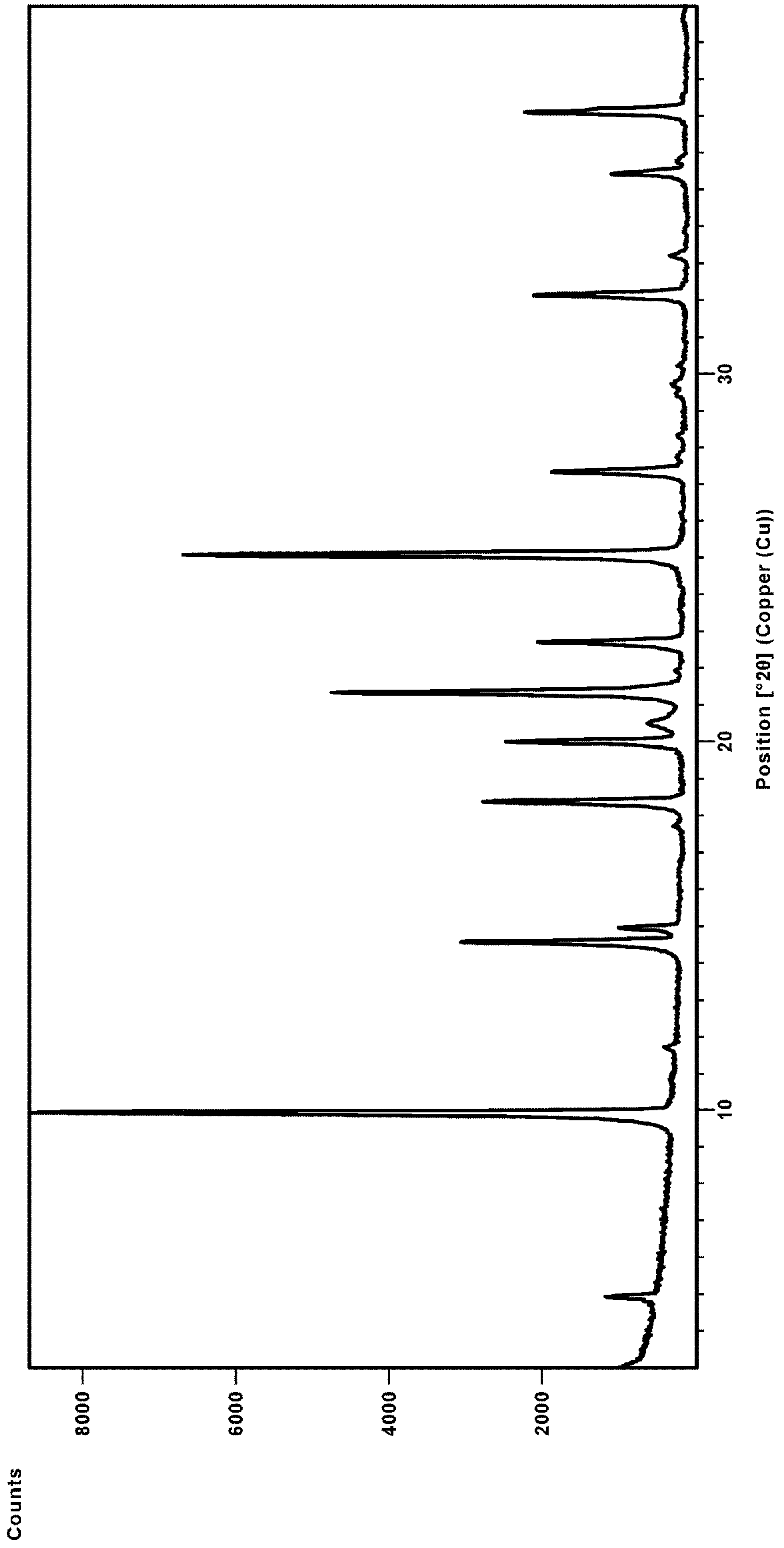
FIG. 1 is a graph of the PXRD pattern of compound A form A, Cu Ka radiation of Position [°2Θ] (Copper (Cu)) vs. counts.

The carboxylic acid halides of formula II and the amines of formula III are either commercially available or can be prepared, for example, according to R. C. Larock, Comprehensive Organic Transformations, Verlag Wiley-VCH, 2nd Edition 1999, pages 1929 ff.

According to the invention, the reaction vessel is initially charged with the carboxylic acid halide of formula II in the solvent, then the desired pressure is established, and the amine III is metered in. Metered addition is understood to mean both the addition in portions and the continuous addition of amines of formula III, a) to the surface of the solution of II, or b) directly into the solution of II.

Carboxylic acid chloride II and amine III are used in about equimolar amounts, or one of the components is used in a slight excess of up to 10 mol %. The molar ratio of III to II is thus generally from 0.9:1 to 1.1:1, preferably from about 1:1 to 1:1.1.

The metered addition of amine III, which is preferably dissolved in the solvent in which acid halide II has also been initially charged, is effected typically over the course of from 0.1 minutes to 5 hours, preferably 5 minutes to 2 hours, more preferably 5 minutes to 30 minutes, particularly 10 minutes and 30 minutes. In one aspect of the present invention the pressure upon addition of the amine and during the course of the reaction until completion is between 30 to 70 kPa.

In a further aspect the pressure upon addition of the amine and during the course of the reaction until completion is between 50 to 70 kPa.

In another aspect the temperature upon addition of the amine and during the course of the reaction until completion is between 20° C. and the temperature that corresponds to the boiling point of the reaction mixture at the given pressure.

In yet another aspect the temperature upon addition of the amine and during the course of the reaction until completion is between 40° C. and the temperature that corresponds to the boiling point of the reaction mixture at the given pressure.

In one aspect of the present invention the pressure upon addition of the amine and during the course of the reaction until completion is between 30 to 70 kPa and the temperature upon addition of the amine and during the course of the reaction until completion is between 40° C. and the temperature that corresponds to the boiling point of the reaction mixture at the given pressure.

In a preferred aspect the solvent is ethyl acetate and the pressure upon addition of the amine and during the course of the reaction until completion is between 30 to 70 kPa, and wherein the temperature upon addition of the amine and during the course of the reaction until completion is between 20° C. and the temperature that corresponds to the boiling point of the reaction mixture at the given pressure.

In a particularly preferred aspect the solvent is ethyl acetate and the pressure upon addition of the amine and during the course of the reaction until completion is between 50 to 70 kPa, and wherein the temperature upon addition of the amine and during the course of the reaction until completion is between 40° C. and the temperature that corresponds to the boiling point of the reaction mixture at the given pressure.

In one embodiment the solvent is selected from the group consisting of ethyl acetate, n-butyl acetate, iso-butyl acetate, iso-propyl acetate, and 3-methyl-butyl acetate (iso-amyl acetate); preferably the solvent is ethyl acetate.

The solvent is used in an amount that is sufficient to dissolve the carboxylic acid halide II. After the reaction has started, eventually the carboxamide of formula I precipitates and forms a slurry.

The amount of solvent should be chosen so as to enable a thorough agitation of the slurry obtained after the addition of the amine III to the acid halide II.

According to a preferred embodiment the solvent is substantially anhydrous. The term “substantially anhydrous” refers to a low water content and is understood to mean from about 0.05 to 1 mol % of water per mole of acid halide II.

Larger amounts of water should be avoided, since the water would lead to an increased consumption of feedstocks.

The carboxamide I is released from the reaction mixture preferably by direct crystallization, crystallization after concentration, or by treatment of the reaction mixture with a suitable base and subsequent crystallization, for example at from −20 to 20° C. Suitable bases for this purpose are alkali metal hydroxides such as sodium and potassium hydroxide, alkali metal carbonates such as sodium and potassium carbonate, alkali metal hydrogencarbonates such as sodium and potassium hydrogencarbonate, alkali metal phosphates such as sodium and potassium phosphate, alkali metal hydrogenphosphates such as sodium and potassium hydrogenphosphate, alkalimetal dihydrogenphosphates such as sodium and potassium dihydrogenphosphate, and also nitrogen bases such as ammonia. Particular preference is given to the alkali metal hydroxides such as sodium and potassium hydroxide, alkali metal carbonates such as sodium and potassium carbonate, and also to the alkali metal hydrogencarbonates such as sodium and potassium hydrogencarbonate.

The base can be used in solid form or in the form of its commercial aqueous solutions. Preference is given to using a from 1 to 20% by weight aqueous solution, the amount preferably being such that the pH of the solution is from 3 to 12, preferably from 7 to 10.

The crystalline product of value can finally be removed by means of customary methods, for example filtration.

In one aspect the present invention relates to a process as defined above, wherein the carboxylic acid halide is of formula II.a,

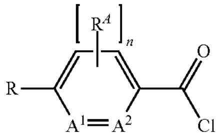

II.a wherein R is cyano or 5-(trifluoromethyl)-1,2,4-oxadiazole-3-yl; n corresponds to the total number of radicals $R^A$ attached to the central aromatic ring and wherein n is 0 or 1; $A^1$ and $A^2$ are independently selected from nitrogen, C—H, or C—$R^A$; and wherein no more than one of $A^1$ and $A^2$ is nitrogen; and wherein $R^A$ is halogen, $C_6$-$C_6$-alkyl, $C_1$-$C_6$-haloalkyl, $C_1$-$C_6$-alkoxy, or $C_1$-$C_6$-haloalkoxy;
with an amine compound of formula III, $HNR^1R^2$ III wherein $R^1$ and $R^2$ are as defined or preferably defined herein for compounds of the formula I, to obtain an aromatic carboxamide of formula I.a,

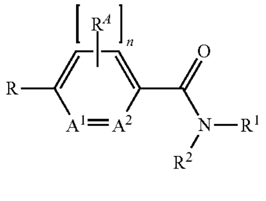

I.a wherein the variables R, n, $R^A$, $A^1$, and $A^2$ have the meaning as defined for compounds II.a; and wherein the variables $R^1$ and $R^2$ have the meaning as defined or preferably defined herein for amine compounds of formula III.

In one aspect of the present invention the variable Aryl is phenyl.

In one embodiment the variables $A^1$ and $A^2$ in compounds of formula I.a and II.a are C—H.

In a preferred embodiment $R^A$ is fluorine.

In one embodiment the variable n is 0.

In a preferred embodiment n is 0 and $A^1$ and $A^2$ in compounds of formula I.a and II.a are C—H.

In a preferred aspect the variable Hal in compounds of formula II is chlorine.

In one aspect the present invention relates to the preparation of compounds of formulae I, I.a, III, IV.a, V.a, VI, and VI.a, wherein $R^1$ is methyl, ethyl, n-propyl, iso-propyl, n-butyl, sec-butyl, iso-butyl, cyclopropyl, 2-methoxyimino-ethyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, methyl, ethyl, methoxy, trifluoromethyl, trifluoromethoxy, difluoromethyl, difluoromethoxy, and cyclopropyl; and $R^2$ is hydrogen, methyl, or ethyl.

In another aspect the present invention relates to the preparation of compounds of formulae I, I.a, III, IV, IV.a, V, V.a, VI, and VI.a, wherein $R^1$ is methyl or phenyl, wherein the phenyl ring is unsubstituted or substituted with 1, 2, 3, or 4 identical or different groups selected from halogen; and wherein $R^2$ is hydrogen, methyl, or ethyl.

In a preferred aspect the present invention relates to the preparation of compounds of formulae I, I.a, III, IV, IV.a, V, V.a, VI, and VI.a, wherein $R^1$ is methyl, 2-fluoro-phenyl, 4-fluoro-phenyl, or 2,4-difluoro-phenyl; in particular methyl or 2-fluoro-phenyl; and wherein $R^2$ is hydrogen.

In a further embodiment the present invention relates to a process to prepare carboxamides of formulae I or I.a as described above, whereas radical R is cyano; and wherein the process further comprises the step of reacting the compounds of formulae I or I.a to obtain amidoximes of formulae IV or IV.a,

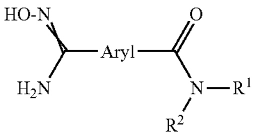

IV

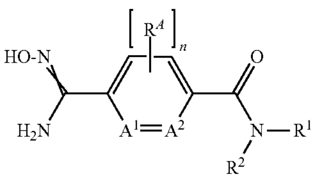

IV.a wherein the variables are as defined or preferably defined herein, by treatment with hydroxylamine or a salt thereof, for example the hydrochloride salt, in the presence of a base, preferably triethylamine, sodium hydroxide or sodium methylate, in a suitable solvent, such as methanol, ethanol, N,N-dimethylformamide, or water, or a mixture of these solvents, at a temperature between 0° C. and 100° C. For related examples see Kitamura, S. et al *Chem. Pharm. Bull.* 2001, 49, 268 or any one of the patent references cited above.

In a further embodiment of the present invention the compounds of formulae IV and IV.a are used to obtain 5-trifluoromethyl-1,2,4-oxadiazoles of formulae V or V.a,

V

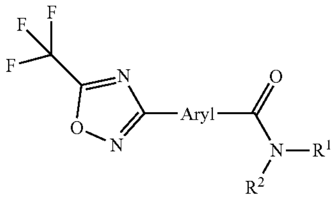

V.a

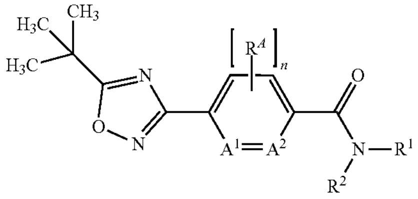

wherein the variables are as defined or preferably defined herein, by treatment with trifluoroacetic acid anhydride or trifluoroacetic acid chloride, in the presence or absence of an organic or inorganic base, for example trimethylamine, triethylamine, diisopropylethylamine, pyridine, 2,4,6-collidine, 2,6-lutidine, 2-picoline, 3-picoline, 4-picoline, 5-ethyl-2-methyl-pyridine, sodium acetate, potassium acetate, sodium carbonate and potassium carbonate; and in a suitable solvent such as toluene, tetrahydrofuran, or dichloromethane, at a temperature between 0° C. and 100° C. For related examples see WO 2015/185485 A1, WO 2017/211649 A1 or WO 2019/020451.

In another embodiment of the present invention the compounds of formulae V and V.a are used to obtain thionylated carboxamides of formulae VI or VI.a,

VI

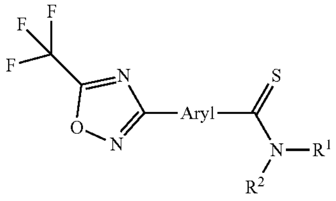

VI.a

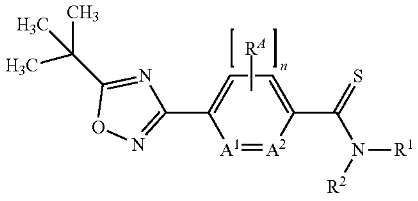

wherein the variables are as defined or preferably defined herein, by treatment with Lawesson's reagent or phosphorus pentasulfide in an inert organic solvent, such as non-halogenated aliphatic hydrocarbons, non-halogenated cycloaliphatic hydrocarbons, halogenated aliphatic hydrocarbons, halogenated aromatic hydrocarbons, amides, ethers, esters, ketones, nitriles; for example toluene, tetrahydrofuran, dioxane or ethyl acetate; at a temperature between 0° C. and 130° C., preferentially between 60° C. and 80° C. For examples, see Eur. J. Med. Chem. 2011, 46(9), 3917-3925; Synthesis 2003, 13, 1929-1958; WO 2006/0123242; WO 2010/086820; WO 2014/0151863. After completion of the reaction the reaction mixture is worked up in the usual manner.

In another embodiment of the present invention the compounds of formulae I or I.a, wherein R is 5-(trifluoromethyl)-1,2,4-oxadiazole-3-yl and wherein Aryl is phenyl or $A^1$ and $A^2$ are C—H, respectively, are used to obtain thionylated carboxamides of formulae VI or VI.a in the same way as described for the thionylation of compounds V and V.a to give thiocaboxamides of formulae VI or VI.a.

In a particularly advantageous three-step approach (reaction scheme below) an amidoxime of formula IV.b is reacted with trifluoroacetic acid chloride (TFACl), in a solvent of formula V as defined or preferably defined herein, to obtain oxadiazole compounds of formula V.b, which are then reacted in a second step with a chlorinating agent, particularly with thionyl chloride, in a solvent of formula V as defined or preferably defined herein, to prepare benzoylchlorides of formula II.b. Example 1 below provides the basis of enablement for this type of transformation. Compounds of formula II.b are then further reacted with an amine of formula III as defined or preferably defined herein, in a solvent of formula V as defined or preferably defined herein, and under the conditions of the present invention, as defined or preferably defined herein, to obtain compounds of type I.b.

This three-step sequence can be conducted using the same solvent of formula V in all three consecutive steps and without the need for changing the reaction vessel between steps, therefore, not requiring the isolation and handling of compounds V.b and II.b. This three-step transformation is particularly preferred in regard to compounds of formula III and I.b, wherein $R^1$ is hydrogen and $R^2$ is 2-fluorophenyl; and wherein the solvent V in all three steps is iso-propyl acetate, n-butyl acetate, or ethyl acetate; particularly the solvent V in all three steps is ethyl acetate; and wherein the pressure in the third step is between 50 to 70 kPa; and wherein the temperature upon addition of the amine and during the course of the reaction until completion is between 40° C. and the temperature that corresponds to the boiling point of the reaction mixture at the given pressure.

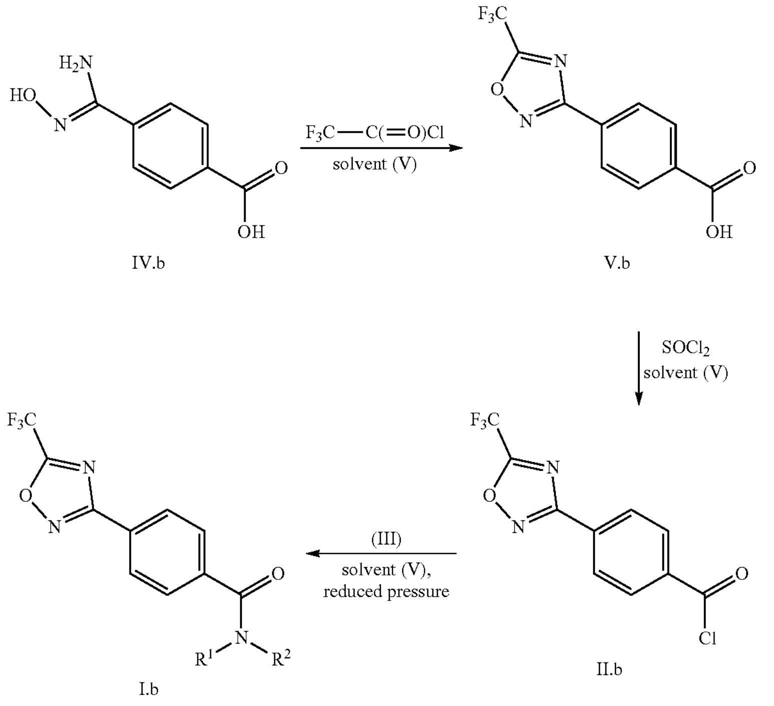

The term "auxiliary base" as used herein refers to a base, which does not take part in the reaction as a reactant but acts as a scavenger for the hydrogen halide, which is formed upon reaction of acid halides of formulae II or II.a with amines of formula III, as defined herein. Non-limiting examples for suitable auxiliary bases are pyridine, triethylamine, or diisopropylethylamine.

In the definitions of the variables given above, collective terms are used which are generally representative for the substituents in question.

The term "$C_n$-$C_m$" indicates the number of carbon atoms possible in each case in the substituent or substituent moiety in question.

The term "halogen" refers to fluorine, chlorine, bromine and iodine.

The term "oxo" refers to an oxygen atom =O, which is bound to a carbon atom or sulfur atom, thus forming, for example, a ketonyl —C(=O)— or sulfinyl —S(=O)— group.

The term "$C_1$-$C_6$-alkyl" refers to a straight-chained or branched saturated hydrocarbon group having 1 to 6 carbon atoms, for example methyl, ethyl, propyl, 1-methylethyl, butyl, 1-methylpropyl, 2-methylpropyl, and 1,1-dimethylethyl.

The term "$C_2$-$C_6$-alkenyl" refers to a straight-chain or branched unsaturated hydrocarbon radical having 2 to 6 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "$C_1$-$C_6$-haloalkyl" refers to a straight-chained or branched alkyl group having 1 to 6 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl.

The term "$C_1$-$C_6$-alkoxy" refers to a straight-chain or branched alkyl group having 1 to 6 carbon atoms (as defined above) which is bonded via an oxygen, at any position in the alkyl group, for example methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy group as defined above, wherein some or all of the hydrogen atoms may be replaced by halogen atoms as mentioned above, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2—C_2F_5$, $OCF_2—C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy.

The terms "phenyl-$C_1$-$C_4$-alkyl or heteroaryl-$C_1$-$C_4$-alkyl" refer to alkyl having 1 to 4 carbon atoms (as defined above), wherein one hydrogen atom of the alkyl radical is replaced by a phenyl or hetereoaryl radical respectively.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_4$-alkylthio-$C_1$-$C_4$-alkyl" refers to alkyl having 1 to 4 carbon atoms (as defined above), wherein one hydrogen atom of the alkyl radical is replaced by a $C_1$-$C_4$-alkylthio group.

The term "$C_1$-$C_6$-alkylthio" as used herein refers to straight-chain or branched alkyl groups having 1 to 6 carbon atoms (as defined above) bonded via a sulfur atom. Accordingly, the term "$C_1$-$C_6$-haloalkylthio" as used herein refers to straight-chain or branched haloalkyl group having 1 to 6 carbon atoms (as defined above) bonded through a sulfur atom, at any position in the haloalkyl group.

The term "$C_1$-$C_4$-alkoxyimino" refers to a divalent imino radical ($C_1$-$C_4$-alkyl-O—N═) carrying one $C_1$-$C_4$-alkoxy group as substituent, e.g. methylimino, ethylimino, propylimino, 1-methylethyl-imino, butylimino, 1-methylpropylimino, 2-methylpropylimino, 1,1-dimethylethylimino and the like.

The term "$C_1$-$C_6$-alkoxyimino-$C_1$-$C_4$-alkyl" refers to alkyl having 1 to 4 carbon atoms, wherein two hydrogen atoms of one carbon atom of the alkyl radical are replaced by a divalent $C_1$-$C_6$-alkoxyimino radical ($C_1$-$C_6$-alkyl-O—N═) as defined above.

The term "$C_2$-$C_6$-alkenyloxyimino-$C_1$-$C_4$-alkyl" refers to alkyl having 1 to 4 carbon atoms, wherein two hydrogen atoms of one carbon atom of the alkyl radical are replaced by a divalent $C_2$-$C_6$-alkenyloxyimino radical ($C_2$-$C_6$-alkenyl-O—N═).

The term "$C_2$-$C_6$-alkynyloxyimino-$C_1$-$C_4$-alkyl" refers to alkyl having 1 to 4 carbon atoms, wherein two hydrogen atoms of one carbon atom of the alkyl radical are replaced by a divalent $C_2$-$C_6$-alkynyloxyimino radical ($C_2$-$C_6$-alkynyl-O—N═).

The term "hydroxy$C_1$-$C_4$-alkyl" refers to alkyl having 1 to 4 carbon atoms, wherein one hydrogen atom of the alkyl radical is replaced by a OH group.

The term "amino$C_1$-$C_4$-alkyl" refers to alkyl having 1 to 4 carbon atoms, wherein one hydrogen atom of the alkyl radical is replaced by a $NH_2$ group.

The term "$C_1$-$C_6$-alkylamino" refers to an amino group, which is substituted with one residue independently selected from the group that is defined by the term $C_1$-$C_6$-alkyl. Likewise, the term "di$C_1$-$C_6$-alkylamino" refers to an amino group, which is substituted with two residues independently selected from the group that is defined by the term $C_1$-$C_6$-alkyl.

The term "$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a $C_1$-$C_4$-alkyl-NH— group which is bound through the nitrogen. Likewise, the term "di$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a $(C_1$-$C_4$-alkyl$)_2$N— group which is bound through the nitrogen.

The term "aminocarbonyl-$C_1$-$C_4$-alkyl" refers to alkyl having 1 to 4 carbon atoms, wherein one hydrogen atom of the alkyl radical is replaced by a —(C═O)—$NH_2$ group.

The term "$C_3$-$C_{11}$-cycloalkyl" refers to a monocyclic, bicyclic or tricyclic saturated univalent hydrocarbon radical having 3 to 11 carbon ring members that is connected through one of the ring carbon atoms by substitution of one hydrogen atom, such as cyclopropyl ($C_3$H5), cyclobutyl, cyclopentyl, cyclohexyl, cycloheptyl, cyclooctyl, bicyclo[1.1.0]butyl, bicyclo[2.1.0]pentyl, bicyclo[1.1.1]pentyl, bicyclo[3.1.0]hexyl, bicyclo[2.1.1]hexyl, norcaranyl (bicyclo[4.1.0]heptyl) and norbornyl (bicyclo[2.2.1]heptyl).

The term "$C_3$-$C_{11}$-cycloalkyl-$C_1$-$C_6$-alkyl" refers to alkyl having 1 to 11 carbon atoms, wherein one hydrogen atom of the alkyl radical is replaced by a $C_3$-$C_{11}$-cycloalkyl group as defined above.

The terms "—C(═O)—($C_1$-$C_6$-alkyl)" and "—C(═O)—($C_1$-$C_6$-alkoxy)" refer to radicals which are attached through the carbon atom of the —C(═O)— group.

The term "aliphatic" refers to compounds or radicals composed of carbon and hydrogen and which are non-aromatic compounds. An "alicyclic" compound or radical is an organic compound that is both aliphatic and cyclic. They contain one or more all-carbon rings which may be either saturated or unsaturated, but do not have aromatic character.

The terms "cyclic moiety" or "cyclic group" refer to a radical which is an alicyclic ring or an aromatic ring, such as, for example, phenyl or heteroaryl.

The term "and wherein any of the aliphatic or cyclic groups are unsubstituted or substituted with . . . " refers to aliphatic groups, cyclic groups and groups, which contain an aliphatic and a cyclic moiety in one group, such as in, for example, $C_3$-$C_3$-cycloalkyl-$C_1$-$C_4$-alkyl; therefore a group which contains an aliphatic and a cyclic moiety both of these moieties may be substituted or unsubstituted independently of each other.

The term "phenyl" refers to an aromatic ring systems including six carbon atoms (commonly referred to as benzene ring.

The term "heteroaryl" refers to aromatic monocyclic or polycyclic ring systems including besides carbon atoms, 1, 2, 3 or 4 heteroatoms independently selected from the group consisting of N, O and S.

The term "saturated 3- to 7-membered carbocycle" is to be understood as meaning monocyclic saturated carbocycles having 3, 4 or 5 carbon ring members. Examples include cyclopropyl, cyclopentyl, cyclohexyl, cycloheptyl, and the like.

The term "3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms", is to be understood as meaning both, aromatic mono- and bicyclic heteroaromatic ring systems, and also saturated and partially unsaturated heterocycles, for example:

a 3- or 4-membered saturated heterocycle which contains 1 or 2 heteroatoms from the group consisting of N, O and S as ring members such as oxirane, aziridine, thiirane, oxetane, azetidine, thiethane, [1,2]dioxetane, [1,2]dithietane, [1,2]diazetidine;

and a 5- or 6-membered saturated or partially unsaturated heterocycle which contains 1, 2 or 3 heteroatoms from the group consisting of N, O and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and a 7-membered saturated or partially unsaturated heterocycle such as tetra- and hexahydroazepinyl, such as 2,3,4,5-tetrahydro[1H]azepin-1-,-2-,-3-,-4-,-5-,-6- or-7-yl, 3,4,5,6-tetrahydro[2H]azepin-2-,-3-,-4-,-5-,-6- or-7-yl, 2,3,4,7-tetrahydro[1H]azepin-1-,-2-,-3-,-4-,-5-,-6-or-7-yl, 2,3,6,7-tetrahydro[1H]azepin-1-,-2-,-3-,-4-,-5-,-6- or-7-yl, hexahydroazepin-1-,-2-,-3- or-4-yl, tetra- and hexahydrooxepinyl such as 2,3,4,5-tetrahydro[1H]oxepin-2-,-3-,-4-,-5-,-6- or-7-yl, 2,3,4,7-tetrahydro[1H]oxepin-2-,-3-,-4-,-5-,-6- or-7-yl, 2,3,6,7-tetrahydro[1H]oxepin-2-, -3-,-4-,-5-,-6- or-7-yl, hexahydroazepin-1-,-2-,-3- or-4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals.

The term "5- or 6-membered heteroaryl" or the term "5- or 6-membered aromatic heterocycle" refer to aromatic ring systems including besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

WORKING EXAMPLES

The present invention is further illustrated by means of the following working examples.

Analytical Methods:

Quantitative HPLC: the following HPLC method was used to determine the chemical purity of the compounds. Instrument: Shimadzu LC2010; System: Low pressure gradient with PDA detector and auto sampler; mobile Phase A: 0.1% o-Phosphoric acid in water; mobile Phase B: Acetonitrile; flow rate: 1.0 mL/min; run Time: 25 min; col. oven temperature: 20° C.; injection volume: 1.0 μL; wavelength: MaxPlot (220 nm to 400 nm); column: Agilent Phenyl Hexyl column, 50 mm*4.6 mm ID, 1.8μ; standard preparation: weigh 100 mg standard in 100 ml volumetric flask, dissolve in acetonitrile, sonicate if required, dilute up to the mark with acetonitrile; sample preparation: weigh 100 mg sample in 100 mL volumetric flask, dissolve in acetonitrile, sonicate if required, dilute up to the mark with acetonitrile.

Gradient Program:

| Time | Function | Value |
|---|---|---|
| 0.01 | B. Conc. | 14% |
| 16 | B. Conc. | 86% |
| 20 | B. Conc. | 86% |
| 20.01 | B. Conc. | 14% |
| 24.9 | B. Conc. | 14% |
| 25 | CONTROLLER | STOP |

Calculation for Assay of samples by HPLC External Standard Method: % Product=[(Area of Sample/Area of Standard)]×[(Weight of Standard in g×Purity of Std)/Weight of sample in g]

Example 1) Preparation of 4-[5-(trifluoromethyl)-1,2,4-oxadiazol-3-yl]benzoyl chloride

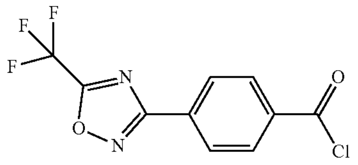 [SMILES: O=C(Cl)c1ccc(-c2noc(C(F)(F)F)n2)cc1]

To a solution of 20 g 4-[5-(trifluoromethyl)-1,2,4-oxadiazol-3-yl]benzoic acid (0.077 mol) in 100 mL ethyl acetate was added 0.2 g of DMF (0.003 mol, 0.03 equivalents) and to this mixture 10.7 g thionyl chloride (0.09 mol, 1.16 eq) was dosed at 75-77° C. during 15 minutes to the reaction mass. Further reaction mass was refluxed for 2.5 h and conversion was checked by quenching a sample in methanol. After completion, ethyl acetate was partly removed so that the residual amount of ethyl acetate was sufficient to keep the reaction product in solution. This reaction medium was directly used in the next step.

Example 2) Preparation of N-(2-fluorophenyl)-4-[5-(trifluoromethyl)-1,2,4-oxadiazol-3-yl]benzamide (Compound A)

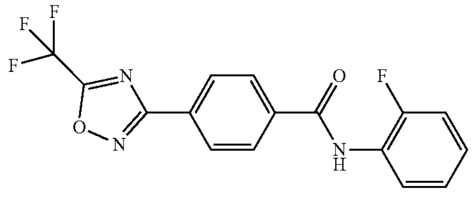 [SMILES: O=C(Nc1ccccc1F)c1ccc(-c2noc(C(F)(F)F)n2)cc1]

The reaction mixture from Example 1 was brought to a temperature of approximately 60° C. and the pressure was reduced to 60 kPa. Under these conditions the reaction mixture started to reflux. Then, 8.64 g 2-fluoroaniline (0.077 mol), dissolved in 20 mL ethyl acetate, was added to the solution of the acid chloride. The reaction mixture was stirred for 1 hours. After cooling the reaction mixture to 0-5° C. compound A was obtained by filtration.

Table A below summarizes the results of a series of experiments, which were conducted as described in Example 2, and in which only the time for the addition of 2-fluoroaniline was varied. The results demonstrate that the title carboxamide was obtained in high yields and high purity and that the addition time has no effect on yield or purity of the reaction.

TABLE A

| Entry | Addition time for 2-F-aniline in minutes | Isolated yield [%] | Purity Quant. HPLC [%] |
|---|---|---|---|
| 1 | 120 | 88.8 | 95.11 |
| 2 | 90 | 90.4 | 96.48 |
| 3 | 60 | 88.2 | 97.06 |
| 4 | 30 | 89.5 | 95.93 |
| 5 | 15 | 89.9 | 95.61 |
| 6 | 1 | 89.9 | 98.01 |

Polymorphism of Compound A

Compound A was obtained as described in example 2) above in crystalline form. This form is herein referred to as form A.

Crystallization

Compound A form A was obtained by evaporation of a homogeneous solution, e.g. from acetone, acetonitrile, dichloromethane, N,N-dimethylformamide, acetic acid, ethyl acetate, methyl ethylketone, methyl iso-butylketone, N-methyl-2-pyrrolidone, pyridine, tetrahydrofuran, 2-butanol, or 1,4-dioxane.

Recrystallization of compound A from ethyl acetate, dioxane, methyl ethylketone led to the formation of compound A form A (cooling rate −5° C./h or cooling by placing in ice bath).

Anti-solvent precipitation from following solvent mixtures (solvent/anti-solvent) also led to the formation of compound A form A: tetrahydrofurane/water, ethyl acetate/n-heptane, dioxane/water, dioxane/n-heptane, methyl ethylketone/n-heptane and acetone/water.

Powder X-Ray Diffraction (PXRD)

The PXRD pattern of compound A form A reference sample is displayed in FIG. 1. Peak positions are listed in Table 1. The PXRD pattern of a second compound A form A (cooling crystallization from ethyl acetate, −5° C./h) is shown in FIG. 2.

FIG. 1: PXRD pattern of compound A form A, Cu $K_\alpha$ radiation.

Figure 2:
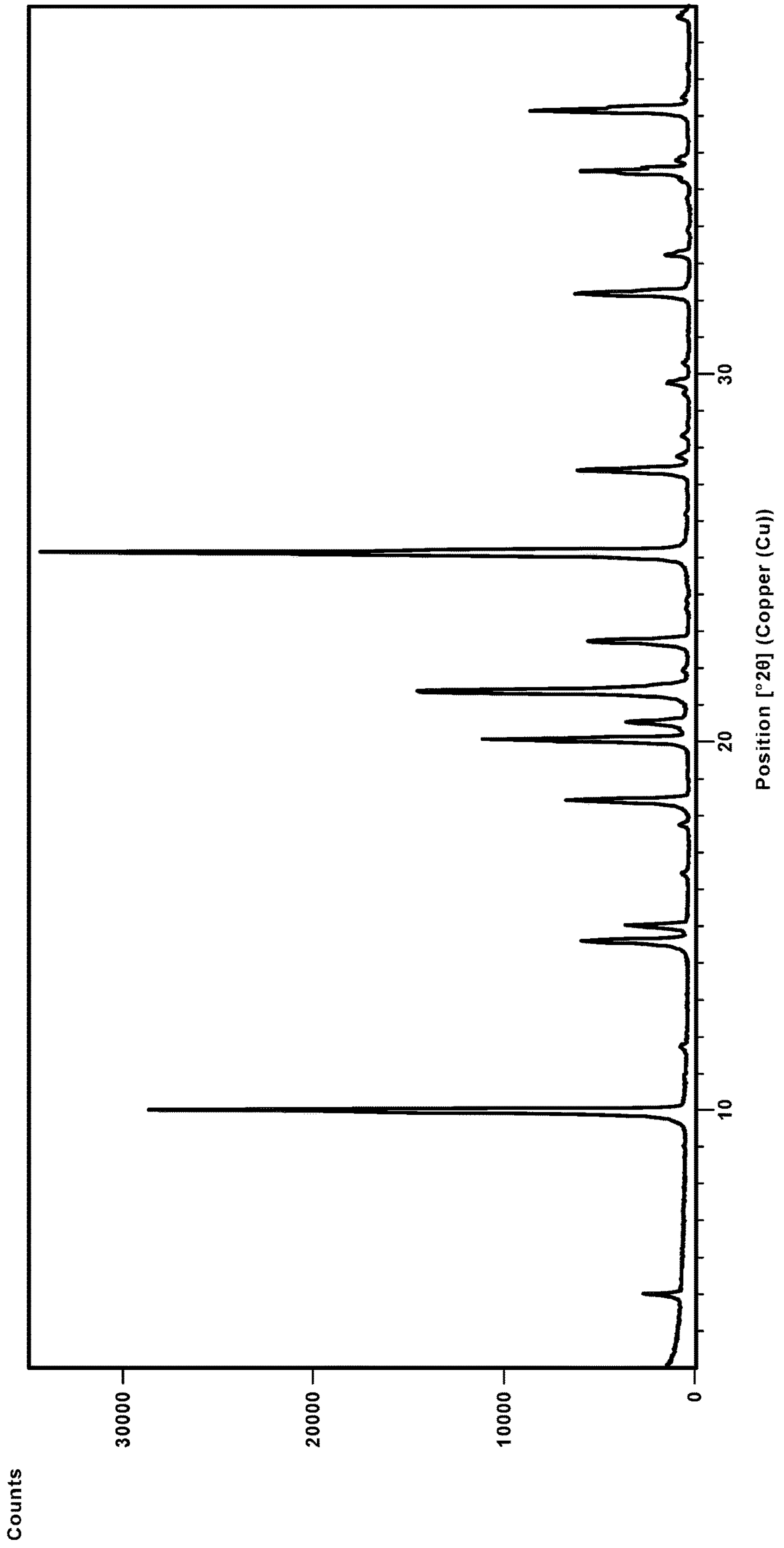
FIG. 2 is a graph of the PXRD pattern of compound A form A (cooling crystallization from ethyl acetate), Cu Ka radiation of Position [°2Θ] (Copper (Cu) vs. counts)

FIG. 2: PXRD pattern of compound A form A (cooling crystallization from ethyl acetate), Cu $K_\alpha$ radiation.

EXPERIMENTAL: POWDER X-RAY DIFFRACTION

Laboratory PXRD patterns were recorded with a PANalytical X'Pert Pro X-ray diffractometer using Cu Kα radiation in reflection geometry (Bragg-Brentano). The sample is placed in a silicon single crystal sample holder of 0.2 mm depth and gently and precisely flattened. The tube voltage is 45 kV and current is 40 mA. The PXRD data are collected at room temperature in the range from 2θ=3.0°-40.0° with increments of 0.017° and measurement time of 20 to 200 s/step.

TABLE 1

X-ray peaks of compound A, form A (Cu $K_\alpha$ radiation)

| peak position [°2θ] | intensity [%] |
|---|---|
| 4.9 ± 0.2 | 7 |
| 9.9 ± 0.2 | 100 |
| 14.6 ± 0.2 | 34 |
| 15.0 ± 0.2 | 9 |
| 18.4 ± 0.2 | 31 |
| 20.0 ± 0.2 | 27 |
| 21.3 ± 0.2 | 55 |
| 22.7 ± 0.2 | 23 |
| 25.1 ± 0.2 | 78 |
| 27.3 ± 0.2 | 21 |
| 32.1 ± 0.2 | 24 |
| 35.4 ± 0.2 | 12 |
| 37.1 ± 0.2 | 25 |

Thermoanalysis

Figure 3:
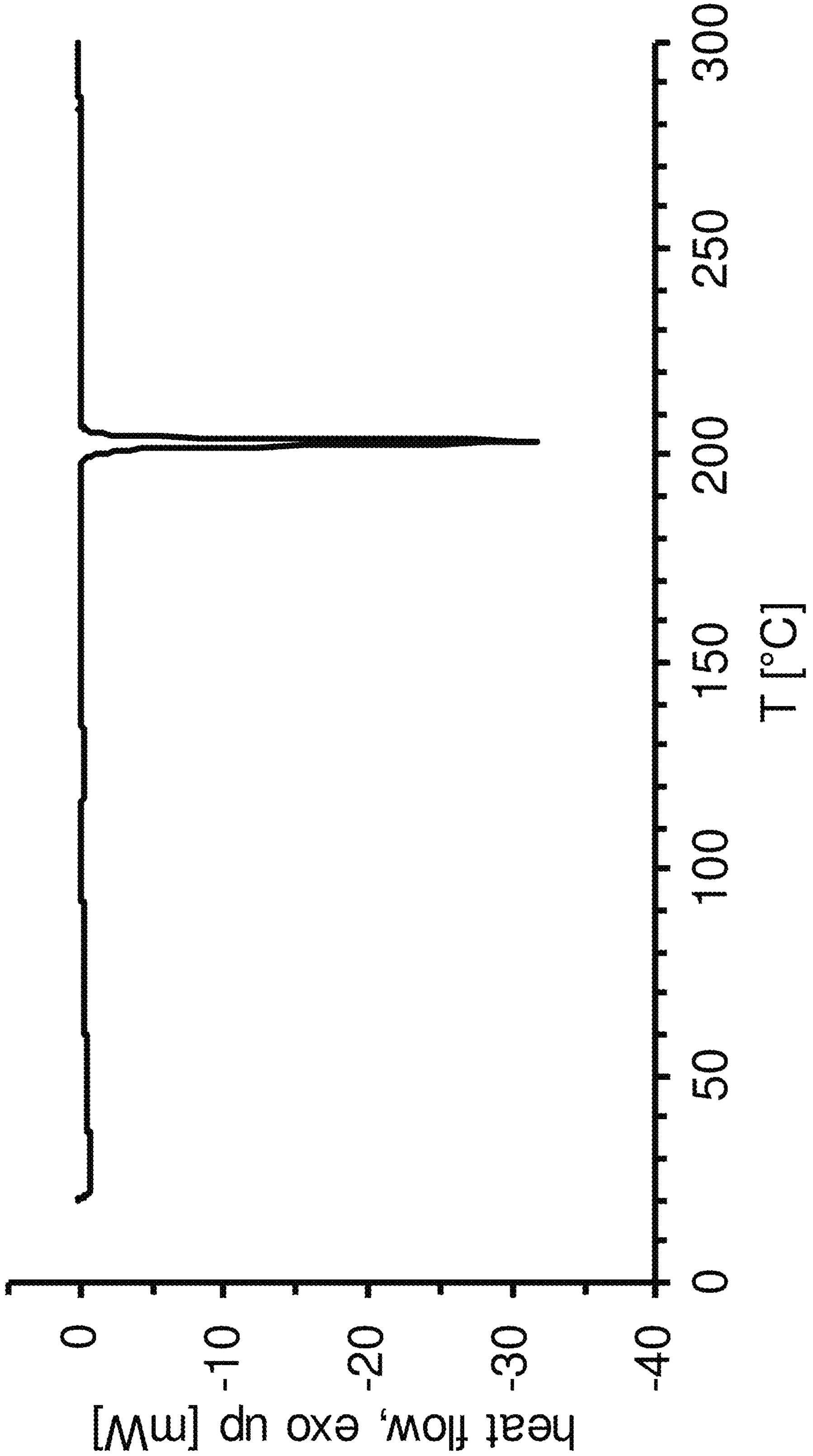
FIG. 3 is a graph of heat flow, exo up [mW] vs. T [° C.] showing the DSC data of compound A form A (heating rate 10° C./min).

The DSC data of compound A form A are displayed in FIG. 3. DSC data show a melting point with an onset of 201° C. and 202° C. peak maximum.

FIG. 3: DSC data of compound A form A, heating rate 10° C./min, exo up.

Experimental: Dynamic Scanning Calorimetry (DSC) DSC data were recorded with a Mettler Toledo DSC 823e/700/229 module. The samples were placed in aluminum standard pans. The sample size in each case was 1 to 10 mg. The heating rate was 10° C./min. The samples were purged with a stream of nitrogen during the experiment. The onset point of the endothermic event is reported as melting point.

The invention claimed is:

1. A process for preparing an aromatic carboxamide of formula I.a,

I.a

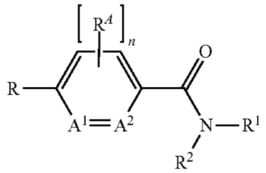

wherein $R^A$ is independently selected from the group consisting of cyano, 5-(trifluoromethyl)-1,2,4-oxadiazole-3-yl, halogen, $C_1$-$C_6$-alkyl, $C_1$-$C_6$-haloalkyl, $C_1$-$C_6$-alkoxy, and $C_1$-$C_6$-haloalkoxy;

R is cyano or 5-(trifluoromethyl)-1,2,4-oxadiazole-3-yl;

n corresponds to the total number of radicals $R^A$ attached to the central aromatic ring and wherein n is 0 or 1;

$A^1$ and $A^2$ are independently selected from nitrogen, C—H, or C—$R^A$; and wherein no more than one of $A^1$ and $A^2$ is nitrogen;

$R^1$ is $C_1$-$C_6$-alkyl, $C_1$-$C_6$-alkoxy, $C_3$-$C_{11}$-cycloalkyl, $C_3$-$C_8$-cycloalkenyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_6$-alkylamino, di$C_1$-$C_6$-alkylamino, —C(═O)—($C_1$-$C_6$-alkyl), —C(═O)—($C_1$-$C_6$-alkoxy), phenyl-$C_1$-$C_4$-alkyl, phenyl-$C_1$-$C_4$-alkenyl, phenyl-$C_1$-$C_4$-alkynyl, heteroaryl-$C_1$-$C_4$-alkyl, phenyl, naphthyl, or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein the heteroaryl group in the group heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O, and S as ring member atoms with the provision that the heterocycle cannot contain 2 contiguous atoms selected from O and S; and wherein any of the above-mentioned aliphatic or cyclic groups are unsubstituted or substituted with 1, 2, 3, or up to the maximum possible number of identical or different groups $R^{1a}$; or $R^1$ and $R^2$, together with the nitrogen atom to which they are attached, form a saturated or partially unsaturated mono- or bicyclic 3- to 10-membered heterocycle, wherein the heterocycle includes beside one nitrogen atom and one or more carbon atoms no further heteroatoms or 1, 2 or 3 further heteroatoms independently selected from N, O, and S as ring member atoms with the provision that the heterocycle cannot contain 2 contiguous atoms selected from O and S; and wherein the heterocycle is unsubstituted or substituted with 1, 2, 3, 4, or up to the maximum possible number of identical or different groups $R^{1a}$; wherein $R^{1a}$ is halogen, oxo, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, —$NHSO_2$-$C_1$-$C_4$-alkyl, (C═O)-($C_1$-$C_4$-alkyl), C(═O)-($C_1$-$C_4$-alkoxy), $C_1$-$C_6$-alkylsulfonyl, hydroxy$C_1$-$C_4$-alkyl, C(═O)-$NH_2$, C(═O)-NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl, or $C_1$-$C_4$-alkoxy-$C_1$-$C_4$-alkyl;

$R^2$ is hydrogen, $C_1$-$C_6$-alkyl, $C_2$-$C_6$-alkenyl, $C_2$-$C_6$-alkynyl, $C_1$-$C_6$-alkoxy, $C_3$-$C_{11}$-cycloalkyl, —C(═O)H, —C(═O)-($C_1$-$C_6$-alkyl), —C(═O)-($C_3$-$C_{11}$-cycloalkyl), or —C(═O)-($C_1$-$C_6$-alkoxy); and wherein any of the aliphatic or cyclic groups in $R^2$ are unsubstituted or substituted with 1, 2, 3, or up to the maximum possible number of identical or different radicals selected from the group consisting of halogen, hydroxy, oxo, cyano, $C_1$-$C_6$-alkyl, $C_1$-$C_6$-alkoxy, and $C_3$-$C_{11}$-cycloalkyl;

the process comprising:

step 1: charging a reaction vessel with a solvent and an aromatic carboxylic acid chloride of formula II.a, II.a

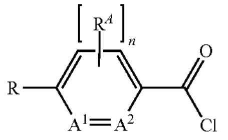

step 2: establishing a pressure of from 10 to 70 kPa in the reaction vessel;

step 3: metering in an amine compound of formula III, $HNR^1R^2$ III;

whereas the process is conducted in the absence of an auxiliary base and is characterized in that the solvent is selected from a carboxylic acid ester of formula V, $R^X$-C(═O)—O—$R^Y$ V wherein $R^X$ is methyl, ethyl, or propyl; $R^Y$ is $C_1$-$C_6$-alkyl, to obtain the aromatic carboxamide of formula I.a, I.a

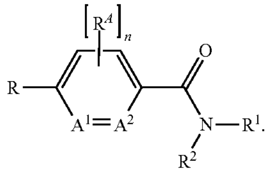

2. The process according to claim 1, wherein $A^1$ and $A^2$ are C—H.

3. The process according to claim 1, wherein n is 0.

4. The process according to claim 1, wherein in the amine compound of formula III, $R^1$ is methyl or phenyl, wherein the phenyl ring is unsubstituted or substituted with 1, 2, 3, or 4 identical or different groups selected from halogen; and wherein $R^2$ is hydrogen, methyl, or ethyl.

5. The process according to claim 1, wherein the amine compound of formula III is used in an amount of 0.9 to 1.1 equivalents based on the carboxylic acid chloride of formula II.a.

6. The process according to claim 1, wherein the pressure upon addition of the amine compound of formula III and during the course of the reaction until completion is between 30 to 70 kPa.

7. The process according to claim 1, wherein the temperature upon addition of the amine compound of formula III and during the course of the reaction until completion is between 20° C. and the temperature that corresponds to the boiling point of the reaction mixture at the given pressure.

8. The process according to claim 1, wherein the solvent is ethyl acetate.

9. The process according to claim 1, wherein radical R is cyano in the aromatic acid chloride of formula II.a; the process further comprising reacting the compound of formula I.a to obtain a compound of formula IV.a IV.a

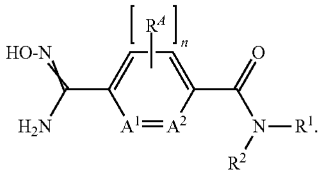

10. The process according to claim 9, further comprising reacting the compound of formula IV to obtain a compound of formula V.a V.a

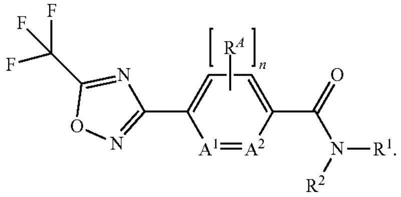

11. The process according to claim 10, further comprising reacting the compound of formula V to obtain a compound of formula VI.a VI.a

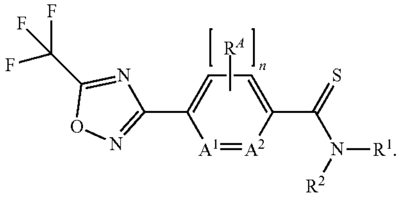

12. The process according to claim 1, wherein R is 5-(trifluoromethyl)-1,2,4-oxadiazole-3-yl; $A^1$ and $A^2$ are C—H; to obtain a compound of formula I.a; the process further comprising reacting the compound of formula I.a to obtain a compound of formula VI.a VI.a

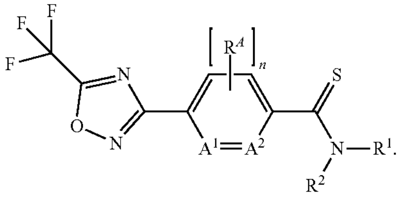

* * * * *